United States Patent
Leatherbury et al.

(10) Patent No.: US 6,514,286 B1
(45) Date of Patent: Feb. 4, 2003

(54) BIODEGRADABLE POLYMERIC FILM

(75) Inventors: Neil C. Leatherbury, San Antonio, TX (US); Kristine Kieswetter, San Antonio, TX (US); Michael A. Slivka, San Antonio, TX (US); Gabriele Niederauer, San Antonio, TX (US)

(73) Assignee: Osteobiologics, Inc., San Antonio, TX (US)

(*) Notice: Subject to any disclaimer, the term of this patent is extended or adjusted under 35 U.S.C. 154(b) by 0 days.

(21) Appl. No.: 09/305,546

(22) Filed: May 5, 1999

Related U.S. Application Data

(63) Continuation of application No. PCT/US97/22552, filed on Dec. 3, 1997.
(60) Provisional application No. 60/032,085, filed on Dec. 3, 1996.

(51) Int. Cl.[7] .................................................. A61F 2/02
(52) U.S. Cl. ................. 623/11.11; 623/6.64; 623/23.59; 623/23.75
(58) Field of Search ................. 623/4.1, 6.64, 623/11.11, 23.75, 23.76, 23.52, 23.59; 606/151, 154, 77

(56) References Cited

U.S. PATENT DOCUMENTS

| | | | |
|---|---|---|---|
| 4,164,794 A | 8/1979 | Spector et al. | 623/23.6 |
| 4,338,926 A | 7/1982 | Kummer et al. | 606/70 |
| 4,655,203 A | 4/1987 | Tömälä et al. | 128/92 YP |
| 4,743,257 A | 5/1988 | Tömälä et al. | 623/16 |
| 4,863,472 A | 9/1989 | Tömälä et al. | 623/16 |
| 4,898,186 A | 2/1990 | Ikada et al. | 606/62 |
| 4,946,467 A | 8/1990 | Ohi et al. | 606/228 |
| 4,968,317 A | 11/1990 | Tömälä et al. | 606/77 |
| 5,118,569 A | 6/1992 | Kuroda et al. | 428/367 |
| 5,189,840 A | 3/1993 | Yanagizawa et al. | 49/493 |
| 5,258,034 A | 11/1993 | Furlong et al. | 623/23 |
| 5,290,494 A * | 3/1994 | Coombes et al. | 264/41 |
| 5,389,412 A | 2/1995 | Tanaka et al. | 428/35.5 |
| 5,403,638 A | 4/1995 | Yanagizawa et al. | 428/90 |
| 5,419,968 A | 5/1995 | Okada et al. | 428/421 |
| 5,496,557 A * | 3/1996 | Feijen et al. | 424/426 |
| 5,584,880 A | 12/1996 | Martinez | 623/4 |
| 5,607,474 A * | 3/1997 | Athanasiou et al. | 623/11 |
| 5,792,400 A | 8/1998 | Talja et al. | 264/103 |
| 5,814,057 A | 9/1998 | Oi et al. | 606/151 |
| 5,861,034 A | 1/1999 | Taira et al. | 623/11 |
| 5,876,452 A * | 3/1999 | Athanasiou et al. | 623/16 |
| 6,162,537 A * | 12/2000 | Martin et al. | 428/373 |

FOREIGN PATENT DOCUMENTS

| | | |
|---|---|---|
| EP | 0 746 270 B1 | 12/1996 |
| WO | WO 94/14390 * | 7/1994 |
| WO | WO 97/13533 | 4/1997 |

OTHER PUBLICATIONS

Andriano, K.P. et al. (1995), "Preliminary Effects of In vitro Lipid Exposure on Absorbable Poly(ortho ester) Films," *J. Appl. Biomat.* 6:129–135.

(List continued on next page.)

*Primary Examiner*—Paul B. Prebilic
(74) *Attorney, Agent, or Firm*—Greenlee, Winner and Sullivan, P.C.

(57) ABSTRACT

This invention provides biodegradable, biocompatible polymeric films having uniform selected thicknesses between about 60 micrometers and about 5 mm useful in the manufacture of therapeutic implants for insertion into a patient's body. The films may be shaped to cover implants made of other materials to improve their biocompatibility. The films may be coated with or incorporate bioactive agents. They may have differing properties, e.g., porosity, thickness, and degradation rate, in different areas.

13 Claims, 1 Drawing Sheet

OTHER PUBLICATIONS

Bawa, R. and Nandu, M. (1990), "Physico–chemical considerations in the development of an ocular polymeric drug delivery system," *Biomaterials* 11:724–728.

Gangadharam, P.R.J., et al. (1991), "Sustained release of isoniazid in vivo from a single implant of a biodegradable polymer," *Tubercle* 72:115–122.

Gangadharam, P.R.J. et al. (1994), "Experimental chemotherapy of tuberculosis using single dose treatment with isoniazid in biodegradable polymers," *J. Antimicrobial Chemotherapy* 33:265–271.

Golomb, G. and Wagner, D. (1991), "Development of a new in vitro model for studying implantable polyurethane calcification," *Biomaterials* 12:397–405.

Hanson, S.J. et al. (1988), "Mechanical Evaluation of Resorbable Copolymers for End Use as Vascular Grafts," *Trans. Am. Soc. Artif. Intern. Organs* 34:789–793.

Johnson, S.D. et al. (1992), "Biocompatibility studies in plasma polymerized interface materials encompassing both hydrophobic and hydrophilic surfaces," *J. Biomed. Materials Res.* 26:915–935.

Levy, F.E., et al., "Effect of a Bioresorbable Film on Regeneration of Cranial Bone," *Plastic and Reconstructive Surgery*, Feb., 1994, 307–311.

Marchant, R.E. et al. (1990), "A hydrophilic plasma polymerized film composite with potential application as an interface for biomaterials," *J. Biomed. Materials Res.* 24:1521–1537.

Melalin, R.J. et al. (1990), "A Biomechanical Study of Tendon Adhesion Reduction Using a Biodegradable Barrier in a Rabbit Model," *J. Appl. Biomat.* 1:13–39.

Mohammed, R. et al. (1987), "The Use of a Biodegradable Collagen/Vicryl Composite Membrane to Repair Partial Nephrectomy in Rabbits", *Urological Res.* 15:239–242.

Monsour, M.J. et al. (1987), "An Assessment of a Collagen/Vicryl Composite Membrane to Repair Defects of the Urinary Bladder in Rabbits," *Urological Res.* 15:235–238.

Morain, W.D., et al. (Dec., 1987), "Reconstruction of Orbital Wall Fenestrations with Polyglactin 910 Film," *Plastic and Reconstructive Surgery*, 769–774.

Schliephake, H. et al. (1994), "Enhancement of Bone Ingrowth into a Porous Hydroxylapatite–Matrix Using a Resorbable Polylactic Membrane," *J. Oral and Maxillofacial Surg.* 52:57–63.

Schönherr, E. et al. (1995),"Decorin–Type I Collagen Interaction," *J. Biological Chemistry* 270(15):887–8883.

\* cited by examiner

BIODEGRADABLE POLYMERIC FILM

This application is a continuation application of PCT Application PCT/US97/22552 designating the United States, filed Dec. 3, 1997 and claiming priority to U.S. Provisional Application No. 60/032,085 filed Dec. 3, 1996.

FIELD OF THE INVENTION

This invention is in the field of biodegradable, biocompatible polymeric materials, suitable for implantation into a patient's body.

BACKGROUND OF THE INVENTION

Many substances used for implants, such as osteochondral implants and orbital implants, e.g., made of hydroxylapatite, are rough and can cause injury to surrounding tissue or interfere with articulation. Smooth implants, however, do not allow for tissue ingrowth and muscle attachment as well as would be desired.

Polymeric films have been used in several types of medical applications in connection with implants. Colomb, G. and Wagner, D. (1991), "Development of a new in vitro model for studying implantable polyurethane calcification," Biomaterials 12:397–405, discloses the use of non-biodegradable polyurethane films 0.2 to 0.7 mm thick to study implant calcification. Bawa, R. and Nandu, M. (1990), "Physico-chemical considerations in the development of an ocular polymeric drug delivery system," Biomaterials 11:724–728, discloses the use of non-biodegradable silicone-based prepolymer films impregnated with gentamicin sulfate for the fabrication of ocular devices. Marchant, R. E. et al. (1990), "A hydrophilic plasma polymerized film composite with potential application as an interface for biomaterials," J. Biomed. Materials Res. 24:1521–1537, discloses plasma deposition of a first layer polymerized from n-hexane and a second layer polymerized from N-vinyl-2-pyrrolidone to form a 420 nm thick composite film on a non-organic substrate providing a non-cytotoxic covering. Johnson, S. D. et al. (1992), "Biocompatibility studies in plasma polymerized interface materials encompassing both hydrophobic and hydrophilic surfaces," J. Biomed. Materials Res. 26:915–935, discloses that thin plasma-deposited films (about 1 micrometer thick) made from N-vinyl-2-pyrrolidone, $\gamma$-butyrolactone, hexamethyldisilazane and n-hexane on biomaterials provide good compatibility (reduced toxicity). Plastic and Reconstructive Surgery, December, 1987, 769–774, discloses the use of bioabsorbable Polyglactin 910 (Vicryl®) film implants for treatment of orbital wall wounds. The film was completely degraded within four months. The films were not seen to affect bone regrowth when compared to controls without the films, but were used to prevent herniation of orbital contents. The film was not used as a covering for another implant material to promote bone or muscle ingrowth. The film did not cause a long-standing inflammatory reaction as did a Dacron-reinforced silicone film to which it was compared. The Polyglactin 910 film used was 0.125 mm (125 micrometers) in thickness. Polyglactin 910 is a 10:90 PLA:PGA polymer film.

Use of a biodegradable polylactic acid (PLA) film 150 micrometers thick was reported in Levy, F. E., et al., "Effect of a Bioresorbable Film on Regeneration of Cranial Bone," Plastic and Reconstructive Surgery, February, 1994, 307–311. After 24 weeks cranial defects covered with the film showed improved healing compared with untreated controls.

Gangadharam, P. R. J. et al. (1994), "Experimental chemotherapy of tuberculosis using single dose treatment with isoniazid in biodegradable polymers," J. Antimicrobial Chemotherapy 33:265–271 discloses the use of a PLA:PGA film containing isoniazid to provide sustained release of the drug for up to four weeks. Details of the preparation of the polymeric film are provided in Gangadharam, P. R. J., et al. (1991), "Sustained release of isoniazid in vivo from a single implant of a biodegradable polymer," Tubercle 72:115–122. The film was a 90% lactic/10% glycolic acid polymer having an average polymer molecular weight of 35,000 Daltons. Films containing the drug were prepared by dissolving the polymer in methyl chloride and passing the solution through an 0.8 mm Millipore filter. The drug was added to the solution and the solution was cast onto a clean glass surface as a thin film 0.6 mm in thickness, then air dried, followed by vacuum drying at 45° C.

Melalin, R. J. et al. (1990), "A Biomechanical Study of Tendon Adhesion Reduction Using a Biodegradable Barrier in a Rabbit Model," J. Appl. Biomat. 1:13–39, disclosed the use of a knitted cellulose material to reduce adhesion formation.

Monsour, M. J. et al. (1987), "An Assessment of a Collagen/Vicryl Composite Membrane to Repair Defects of the Urinary Bladder in Rabbits," Urological Res. 15:235–238, and Mohammed, R. et al. (1987), "The Use of a Biodegradable Collagen/Vicryl Composite Membrane to Repair Partial Nephrectomy in Rabbits", Urological Res. 15:239–242, discloses a collagen-coated vicryl mesh to facilitate surgical healing. Andriano, K. P. et al. (1995), "Preliminary Effects of In vitro Lipid Exposure on Absorbable Poly(ortho ester) Films," J. Appl. Biomat. 6:129–135, discloses poly(ortho ester) film degradation in vitro in cholesterol emulsions. Hanson, S. J. et al. (1988), "Mechanical Evaluation of Resorbable Copolymers for End Use as Vascular Grafts," Trans. Am. Soc. Artif. Intern. Organs 34:789–793, discloses the use of PLA/$\epsilon$-caprolactone materials as vascular graft materials.

None of the foregoing references disclose such films molded or shaped to surround implants made of other materials to improve the biocompatibility of such implants.

Schliephake, H. et al. (1994), "Enhancement of Bone Ingrowth into a Porous Hydroxylapatite-Matrix Using a Resorbable Polylactic Membrane," J. Oral and Maxillofacial Surg. 52:57–63, discloses the use of a polylactic membrane (L/DL-Lactic Acid 70/30) to cover hydroxylapatite blocks placed in mandible and ilium defects. The membrane was nearly completely degraded after five months and the blocks covered with membrane showed more bony penetration of the HA matrix compared to blocks not covered by the membrane. The membrane had been replaced by a thin, fibrous scar. The degradation time was reported as being slow enough to prevent connective tissue cells from penetrating into the block pores so as to allow ingrowth of bone tissue from underlying host bone. The membrane was adapted to the block by a prefabricated, heated metal template which, the reference teaches, may be impossible in a situation where an individual contour is needed due to the rigidity of the polylactic material.

U.S. Pat. No. 5,584,880, issued Dec. 17, 1996 to Martinez for "Orbital Implant" discloses an orbital implant comprising hydroxylapatite granules which may be covered by a layer of synthetic material which is preferably a synthetic fabric made of a polymeric material.

None of the foregoing references disclose biodegradable films designed to fit individual contours of implants and to degrade within a short enough period, e.g., less than about four months, to promote rapid muscle and connective tissue attachment to the implant material.

It is therefore an object of this invention to provide biodegradable films which can be used to coat contoured implants, such as rounded hydroxylapatite implants used for orbital reconstruction, or to coat polymeric or other implants to provide improved, smooth articulating surfaces, to improve biocompatibility of the implants and to promote muscle and connective tissue attachment. It is also an object of this invention to provide biodegradable polymeric films designed to have different degradation rates at different locations in the film.

SUMMARY OF THE INVENTION

This invention provides a biodegradable, biocompatible polymeric film having a uniform selected thickness between about 60 micrometers and about 5 mm. Films of between about 600 micrometers and 1 mm and between about 1 mm and about 5 mm thick, as well as films between about 60 micrometers and about 1000 micrometers; and between about 60 and about 300 micrometers are useful in the manufacture of therapeutic implants for insertion into a patient's body. Films between about 60 and about 120 micrometers and between about 75 and about 125 micrometers are also useful in this invention.

The term "biodegradable" means capable of breaking down over time inside a patient's body. A number of suitable biodegradable polymers for use in making the materials of this invention are known to the art, including polyanhydrides and aliphatic polyesters, preferably polylactic acid (PLA), polyglycolic acid (PGA) and mixtures and copolymers thereof, more preferably 50:50 copolymers of PLA:PGA and most preferably 75:25 copolymers of PLA:PGA. Single enantiomers of PLA may also be used, preferably L-PLA, either alone or in combination with PGA. Polycarbonates, polyfumarates and caprolactones may also be used to make the implants of this invention. The film degradation period should be short enough to allow muscle and connective tissue attachment to the underlying implant, e.g., less than about four months, preferably between about one and about ten weeks and, in some cases, between about one and about three weeks, or no more than about four weeks.

The term "biocompatible" as used herein with respect to a polymeric film means that the degradation of the film does not elicit an adverse biologic response, that its surfaces are smooth rather than rough or abrasive, and that it is "substantially free" of most residual solvents, such as acetone, meaning that insufficient solvent is present in the film to interfere with cell implantation on or in the implant. Preferably, the film has less than 100 ppm residual solvent. In some cases, where biocompatible solvents such as N-methyl-pyrrolidone (NMP) are used, making the implant substantially solvent-free is not essential.

The polymeric films of this invention are thin compared to their length and breadth, preferably between about 60 micrometers and 5 mm thick. Large, continuous films may be made by the methods of this invention. Typically, sizes of about 11"×15" can be made. The polymeric films are uniform in thickness, i.e. not varying in thickness by more than about 30 micrometers. The desired thickness of the film may be selected in advance and controlled in the manufacturing process. These large films can be cut or punched to wafer size, e.g., as described in PCT Publication WO 97/13533 published Apr. 17, 1997, incorporated herein by reference to the extent not inconsistent herewith.

The films are not necessarily flat; they may be shaped or contoured to conform to complex implant contours. Contoured films may be spherical, curved and/or have depressions and bulges and may be designed to fit irregularly-shaped implants including tubular (lumenal) implants.

Bioactive agents such as enhancers of cell attachment, growth factors, enzymes, degradation agents, pH-adjusting agents, therapeutic agents, such as antibiotics, analgesics, chemotherapeutic agents, and the like may be used in conjunction with the polymeric films of this invention. For example, the polymeric films of this invention may be coated by means known to the art with a biologically active agent. Alternatively, such bioactive agents may be incorporated into the thin film by means known to the art. See, e.g., U.S. Pat. No. 6,013,853 or U.S. Pat. No. 5,876,452, incorporated herein by reference to the extent not inconsistent herewith. Such agents, which facilitate attachment of cells to the polymeric material are termed "cell attachment enhancers" herein. In addition agents promoting production of various necessary factors within bone, cartilage, muscle or other tissue may be provided, and are included within the term "growth factors" herein. Other suitable bioactive agents and methods for their incorporation into biodegradable polymeric materials are known to the art and disclosed, e.g. in U.S. Pat. No. 6,013,853 or U.S. Pat. No. 5,876,452.

A particularly useful growth factor for use in connection with implants designed to encourage cartilage growth, such as osteochondral implants, is P15, a 15 amino acid, MW 1393.6, polypeptide produced by Peptide Innovations, Inc., Southfield, Mich.

The amount of bioactive agent to be incorporated into or coated on the polymeric films of this invention is an amount effective to show a measurable effect in improving the performance of the film-covered implant, as may be known to the art or determined by testing the film-covered implant with and without the bioactive agent and measuring at least one characteristic to be improved.

The films of this invention are used to at least partially wrap or cover therapeutic implants for placement in the body of a patient. The "patient" can be any living organism, including a warm-blooded mammal, and preferably, a human. Covering an implant with a film of this invention provides a smooth surface to avoid abrasion and damage to neighboring tissue, provides a smooth articulating surface, and provides sites for cell ingrowth and attachment. In addition, for highly porous implants, covering with the polymeric films of this invention provides a continuous surface.

In a preferred embodiment, thin films of this invention are used to cover ocular implants, such as those made of hydroxylapatite. The hydroxylapatite is rough, and the smooth surface of the polymer film covering makes the implant more biocompatible in that it is more easily and comfortably implanted and causes less irritation. As the film degrades over a selected period of time, preferably about one to ten weeks, muscle grows into and attaches to the surface of the implant to allow tracking of the artificial eye.

The polymeric films of this invention can also be used to coat metallic implants, such as titanium jaw implants, to facilitate integration of the implant. Portions of the film may be completely degraded over different time periods, as required by the ingrowth of different tissue. Portions of the underlying implant may be left bare, or the film may have holes produced in it so that muscle and/or connective tissue can be attached to the underlying implant by suturing or other means known to the art.

The polymeric films of this invention may be used to provide a thin coating, preferably a PLG coating about 75 to 125 micrometers in thickness on the articulating portion of a single or multiphase osteochondral or chondral implant, for example as described in U.S. Pat. No. 5,607,474, incorporated herein by reference to the extent not inconsistent herewith. The purpose of this coating is to provide a smooth articulating surface on the open celled, cut surface of a wafer such as a polymeric wafer used as an implant. To attach the film, it is merely "glued" on by wetting the implant with acetone or other suitable solvent and then firmly pressing the film onto it. This coating can be altered as described herein to have various degradation rates and thicknesses and may have a bioactive agent incorporated.

The polymeric films of this invention may be made porous or semi-permeable by known foaming techniques or incorporation of porogenic materials such as leachable salts or laser etching. For example, films which allow passage of nutrients but not cells, having pore sizes between about 0.1 micrometers and about 4 micrometers, can be made by laser etching.

A plasticizer may be incorporated in the biodegradable film to make it softer and more pliable for applications where direct contact with a contoured surface is desired. The thin film is plasticized in solutions of N-methyl-pyrrolidone (NMP) or other biocompatible solvent which can be mixed with a co-solvent such as water, ethanol, PEG-400, glycerol, or other co-solvents known to the art. The co-solvent is required to prevent complete dissolution of the polymer. The film is immersed in the solution until as soft as desired, i.e., soft enough to readily conform to the shape of an implant.

The polymeric films of this invention can be formed and used as flat sheets, or can be formed into three-dimensional conformations or "shells" molded to fit the contours of a specific implant. For example, to cover ocular implants which are spherical in form, polymeric films of this invention can be formed in two hemispheres. The implant can be encapsulated in two halves and the coating fused to form a continuous coating. The films may also be molded or pressed, using heat for softening, into more complicated contours. The film is also provided as a plasticized sheet for use at the time of implantation. A biocompatible solvent as described above makes the film capable of being easily stretched to form around a contoured surface of the implant. The film adheres to itself and can be stretched up to about 200% without tearing. Prior to implantation of the sterile implant, it can be "wrapped" with the plasticized film.

The films of this invention can be designed so that they degrade at different rates in different zones (areas) of the film and/or release or incorporate different bioactive agents in different zones. Porosities, thickness and other properties may also be varied in different zones. This may be desirable so that surface areas of an implant at attachment zones for muscle or other tissue can be made more rapidly degradable and/or porous, while surface areas not required for immediate tissue ingrowth can be made more slowly degradable and/or thicker to provide controlled release of an incorporated bioactive agent. Additionally, implant surfaces near the exterior of the body can be made less rapidly degradable and/or porous to provide better protection against bacterial attack, while inner surfaces can be made more rapidly degradable and/or porous to encourage tissue ingrowth.

DETAILED DESCRIPTION OF THE PREFERRED EMBODIMENTS

Figure 1:
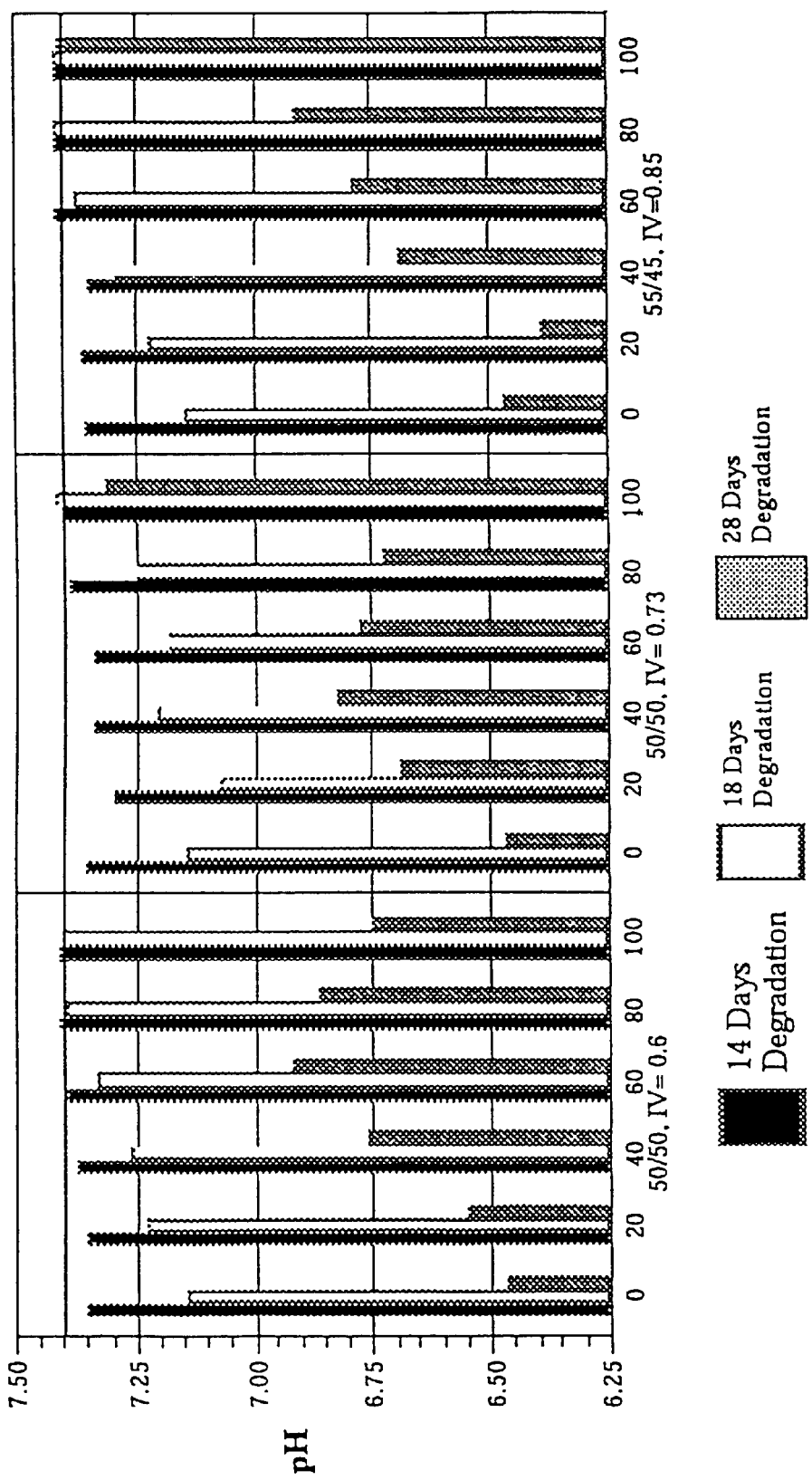
FIG. 1 graphs pH changes, indicating degradation and molecular weight changes, for various polymer blends immersed in phosphate buffered saline (PBS).

Polymeric films of this invention are useful for providing biocompatible coverings for surgical implants. For covering hip implants or rods, films of up to about 5 mm in thickness are suitable. For covering hydroxylapatite ocular implants films of about 60 to about 1000 micrometers are preferred. Films between about 60 and about 300 micrometers are also useful. Films between about 75 and about 125 micrometers in thickness are useful for covering articulating surfaces of implants such as osteochondral or chondral implants. Thicker films of this invention are useful for coverings for extremely rough implant surfaces, to provide extended degradation times, or to accommodate a high degree of porosity for facilitation of tissue ingrowth.

To make the polymeric films of this invention, a suitable polymeric material is selected, depending on the degradation time desired for the film. Selection of such polymeric materials is known to the art. For example PLA is used when a lengthy degradation time is desired, e.g. up to about two years. For the purposes of this invention, shorter degradation times are desired. A low molecular weight, e.g., around 20,000 daltons, 50:50 or 55:45 PLA:PGA copolymer is used when an approximately two-week degradation time is desired. In a preferred embodiment, a 75:25 PLA:PGA copolymer is used, giving a film degradation time of about 8–15 weeks. To ensure a selected degradation time, the molecular weights and compositions may be varied as known to the art.

The degradation of PLA and PGA has been extensively studied, both in vivo and in vitro. A number of factors affect the degradation rate of PLA:PGA copolymers, such as molecular weight, copolymer ratio, polymer crystallinity, thermal history, shape and porosity, and wettability. Additionally, other factors such anatomical site of implant, vascularity, tissue interaction and patient response affect the degradation rate in vivo. Depending on the above listed factors, degradation rates for PLA and PGA polymers have been reported as low as 7 days for 50:50 PLG to several years for PLA. The overall degradation kinetics have been fairly well established for the entire family of homopolymers and copolymers. Table 1, below, summarizes the findings of the degradation rates of the copolymers. Since this table is a compilation of many studies, the broad degradation range is reflective of the different experimental variables and parameters utilized.

TABLE 1

Degradation rates of polymers

| PLA/PGA | Degradation Time |
| --- | --- |
| 100/0 | 24 weeks-over 4 years |
| 85/15 | 12–34 weeks |
| 75/25 | 4–20 weeks |
| 70/30 | 25–30 weeks |
| 50/50 | 1–8 weeks |
| 0/100 | 8–20 weeks |

The molecular weight of the polymer selected is preferably between about 70 and 120 kD; however, higher molecular weights, up to about 600 kD, can be used up to the point where viscosity of the solution prevents even spreading over a surface leading to films of non-uniform thickness. Lower molecular weights may also be used, down to about 5 kD, to the point where the resultant film becomes too brittle to be used.

H-series PLG, a PLG polymer modified to provide acidic carboxy terminals on the polymer chains which makes the polymer more hydrophilic and therefore more easily degraded in an aqueous environment, may be blended with various PLG polymers to provide a film degrading at any desired rate.

The film may be used for surgical attachment of muscles, as for ocular implants, where the surgeon may suture through the film for muscle attachment.

Films of this invention may be porous or nonporous, preferably nonporous.

The films may be used to cover non-biodegradable implants of virtually any type, e.g., those made of hydroxylapatite, titanium, silicon, ceramics, PVC and other polymers, or biodegradable implants such as PLA:PGA implants as described, e.g., in U.S. Ser. No. 08/540,788, incorporated herein by reference. The implants may be, for example, ocular or other organ implants, or those suited for orthopaedic uses of all kinds including femoral, hip, joint, or other implants as known to the art.

Polymeric films of this invention may be made by dissolving the selected polymeric material in a solvent known to the art, e.g. acetone, chloroform or methylene chloride, using about 20 ml solvent per gram of polymer. The solution is then degassed, preferably under gentle vacuum to remove dissolved air and poured onto a surface, preferably a flat non-stick surface such as BYTAC (Trademark of Norton Performance Plastics, Akron, Ohio) non-stick coated adhesive-backed aluminum foil, glass or TEFLON® Non-stick polymer. The solution is then dried, preferably air-dried, until it is no longer tacky and the liquid appears to be gone. The known density of the polymer may be used to back-calculate the volume of solution needed to produce a film of the desired thickness.

To make the film biocompatible, residual solvent which interferes with cell implantation must be removed. Preferably this is done by incubating the dried polymer at about 55–65° C. to drive off residual solvent. A vacuum oven may then be used at about 55–70° C. to remove the final solvent, so that the finished polymeric film has a residual solvent concentration of less than about 100 ppm. The film is then peeled away from the non-stick surface, and is substantially uniform in thickness, smooth, tough, and durable.

Films of this invention may also be made by heat pressing and melt forming/drawing methods known to the art. For example, thicker films can be pressed to form thinner films, and can be drawn out after heating and pulled over forms of the desired shapes, or pulled against a mold by vacuum pressure.

As discussed above, films may be produced wherein different zones of the film have different properties, e.g., different degradation rates, thicknesses, bioactive agents and the like which could affect tissue ingrowth and cell attachment, drug-release kinetics and the like. To make films having different characteristics in different zones, separate films, each having the desired properties for a single zone, can be made and cut to shape. The shapes can then be heat-welded together, preferably by overlapping the sections at least about 2 mm and applying gentle pressure at a temperature of about 60° C.

EXAMPLE 1

Preparation of Film

Thin polymeric films of this invention were prepared according to the following protocol.

Thin polymeric films can be prepared by casting from a solvent onto a non-stock surface. For example, in order to prepare a 28 by 38 centimeter film (11"×15") of 100 µm thickness, we perform the following calculation:

$$28 \text{ cm} \times 38 \text{ cm} \times 0.01 \text{ cm} \times 1.30 \text{ g/cm}^3 = 9.34 \text{ grams polymer}$$

$$9.36 \text{ grams} \times 20 \text{ ml acetone/gram} = 187 \text{ ml acetone}.$$

In a TEFLON beaker fitted with a stirbar, the polymer and acetone are combined, covered and allowed to mix for 20 minutes to completely dissolve the polymer. The beaker is then placed in a vacuum desiccator and a vacuum is applied until the solution begins to bubble vigorously. The vacuum is controlled manually to prevent excessive eruption of the fluid. This de-gassing step is carried out for about 3–5 minutes, until the bubbles become large and the bubbling action less vigorous.

The solution is then gently poured out onto a prepared surface. The pouring action should be accomplished in a single, smooth, continuous step so as to avoid introduction of bubbles and surface irregularities. The surface is very level, smooth, and non-stick. For example, an aluminum plate with a square well 28×38 cm machined into the center can be lined with a commercial non-stick material known as Bytac (Norton Performance Plastics, Akron, Ohio) which has an adhesive side which is applied over the surface, to expose a non-stick fluoropolymer side. This mold is made level by using a carpenter's level or a bubble level. Alternatively, the mold can be "floated" in a bath of water to get a level surface. A level mold is critical to achieving a uniform film thickness.

Once the fluid is poured into the prepared mold surface, it is allowed to air-dry undisturbed until it is no longer tacky (4–12 hours). It can then be placed in an incubator or oven at 55–70° C. for up to seven days to drive off the residual acetone. Preferably the oven or incubator can be swept with nitrogen or dry air to exclude moisture. After at least one day in the incubator, the film can be transferred to a vacuum oven at 65° C. to complete the elimination of solvent. This typically takes about 2 to 3 days at less than 1 torr.

The film is then ready to be further processed.

EXAMPLE 2

Preparation of Heat Molded Film

A molded film was prepared according to the following protocol.

Films can be prepared by hot-molding procedures, for example by using a heated press. A 0.5 mm thick film of diameter of 2.25" can be prepared in the following manner.

The amount of material can be calculated as follows:

$$[2.25 \text{ in } (2.54 \text{ cm/in})]^2 / 4 \times 0.05 \text{ cm} \times 1.30 \text{ g/cm3} = 0.53 \text{ g polymer}.$$

The polymer is placed in the well of a 2.25" ID stainless steel piston and cylinder type mold (Carver) and the upper piston placed on top. The assembly is then placed between the heating platens of a 12-ton press (Carver) and a load of 6000 pounds applied (for an internal pressure of about 1500 psi). The platens are then heated to a temperature of about 200° F., while the pressure is maintained should it drop due to polymer fusion. The external surface of the mold is allowed to come to about 175° F., at which point heating is turned off and optionally cooling applied. While the pressure is maintained, the mold is allowed to cool to less than 100° F. before it is removed from the press. The film can then be removed from the mold and further processed if desired. The mold is shaped to produce a film contoured to fit a desired therapeutic implant and is pressed over the implant in sections, with the edges welded together if desired to completely cover the implant.

EXAMPLE 3

Degradation Profiles

Various blends of PLG polymers with H series PLG polymer result in a wide range of degradation profiles. Thin films were fabricated using polymers with various degradation rates to emulate a range of in vivo degradation rates. The following polymers were tested by blending with Boehringer Ingelheim H-series 50/50 H-D,L-PLG, I.V.=0.49 polymer:

50/50 D,L-PLG, intrinsic viscosity (I.V.)=0.60

50/50 D,L-PLG, I.V.=0.73

55/45 D,L-PLG, I.V.=0.85

The polymer blends were prepared by dissolving the specific varying amounts of each polymer as indicated in FIG. 1 in acetone to achieve intimate mixing, then drying under ambient conditions and curing in a vacuum oven. Solvent levels were tested to meet minimum specifications prior to release for further processing. Cured polymer blends were then ground to a fine powder in a MicroMill. Powdered blends were pressed using a Carver heated press by placing the polymer between two sheets of aluminum foil, spreading it evenly over the surface, and transferring to the press. The platens were heated to 250° F. and a force of 20,000 lbf applied for 30–45 seconds to press the film.

Films with a thickness of 60–120 μm were punched to prepare small film disks. Degradation tests of the films were conducted by placing each disc in a glass vial with PBS and storing in a 37° C. incubator. The pH of the solution was measured every 3.5 days for the 4-week experiment duration. The PBS solution was changed weekly and visual observations made.

FIG. 1 shows the pH changes for the various polymer blends during the 28-day experimental procedure. All polymers contain H series 50/50 PLG polymer. The proportion of the second polymer is indicated on the x-axis. For example, the first bars in each set contain 100% H series 50/50 PLG. The second bars in each set contain 80% H series PLG and 20% of the second polymer. The change in the buffer pH is a good indicator of the changes in the molecular weight of the polymer. At two weeks degradation, not much change in buffer pH is observed. At 18 days, lower pH values are observed with increasing content of H-series PLG. At 28 days, a dramatic drop in the pH is seen for the pure H-series PLG, with the effect being less dramatic as the content of the second polymer is increased.

This experiment shows that low molecular weight 50/50 H-series polymer increases the degradation rate of blends of PLGs in proportion to its content, with the pure 50/50 H-series having the most rapid degradation time. The graph verifies that by blending PLGs of various I.V. or degradation rates, polymer compositions with a range of degradation behaviors result.

The invention may be embodied in other specific forms without departing from the spirit or essential characteristics thereof. The present embodiments are therefore to be considered illustrative and not restrictive, the scope of the invention being indicated by the appended claims rather than by the foregoing description, and all changes which come within the meaning and range of equivalency of the claims are therefore intended to be embraced therein.

What is claimed is:

1. A therapeutic device comprising an implant which is at least partially covered with a biodegradable, biocompatible polymeric film which has a uniform selected thickness between about 75 micrometers and about 125 micrometers, and said film is capable of completely degrading in vivo in no more than about four months.

2. The device of claim 1 comprising a hydroxylapatite surface at least partially covered with said film.

3. The device of claim 1 wherein the biodegradable polymeric film is made of a PLA:PGA copolymer.

4. The device of claim 1 wherein the biodegradable polymeric film comprises a PLA:PGA copolymer modified to increase its hydrophilicity.

5. The device of claim 1 wherein the biodegradable polymeric film is substantially free of solvent used in making said film.

6. The device of claim 1 wherein said film is capable of degrading in vivo in no more than about ten weeks.

7. The device of claim 1 wherein said film is capable of degrading in vivo in no more than about four weeks.

8. The device of claim 1 wherein said film comprises a bioactive agent coated thereon or incorporated therein.

9. The device of claim 1 wherein said implant comprises an articulating surface, and wherein said film covers said articulating surface.

10. A therapeutic device comprising an implant which is at least partially covered, as a surface covering, with a biodegradable, biocompatible polymeric film made of a material selected from the group consisting of polylactic acid, polyglycolic acid, enantiomers thereof, copolymers thereof, and mixtures thereof, having more than one zone, said film having a uniform thickness between about 60 micrometers and about 5 mm in each said zone, and having differing properties selected from the group consisting of degradation time, porosity and thickness in different zones.

11. The device of claim 10 wherein said film has different degradation rates in different zones.

12. The device of claim 10 in the form of a three-dimensional contoured shell.

13. A method of using the therapeutic device of claim 10 comprising implanting said implant into a patient's body.

* * * * *